United States Patent
Chhatrala (10) Patent No.: US 12,376,997 B2
(45) Date of Patent: Aug. 5, 2025

(54) ADJUSTABLE LIMB STABILIZATION DEVICE

(71) Applicant: Pankajkumar Chhatrala, Gujarat (IN)

(72) Inventor: Pankajkumar Chhatrala, Gujarat (IN)

(*) Notice: Subject to any disclaimer, the term of this patent is extended or adjusted under 35 U.S.C. 154(b) by 1034 days.

(21) Appl. No.: 17/311,335

(22) PCT Filed: Dec. 5, 2019

(86) PCT No.: PCT/IN2019/050889
§ 371 (c)(1),
(2) Date: Jun. 6, 2021

(87) PCT Pub. No.: WO2020/115769
PCT Pub. Date: Jun. 11, 2020

(65) Prior Publication Data
US 2022/0015953 A1  Jan. 20, 2022

(30) Foreign Application Priority Data
Dec. 6, 2018 (IN) .............................. 201821046255

(51) Int. Cl.
A61F 13/04 (2006.01)
A61F 5/058 (2006.01)

(52) U.S. Cl.
CPC .......... *A61F 13/04* (2013.01); *A61F 5/05841* (2013.01)

(58) Field of Classification Search
CPC .... A61F 13/04; A61F 5/05841; A61F 5/0106; A61F 5/0111; A61F 5/013; A61F 13/10; A61F 5/05; A61F 5/055; A61F 5/058; A61F 5/0118; A61F 5/01; A61F 5/0104
See application file for complete search history.

(56) References Cited

U.S. PATENT DOCUMENTS

2018/0055671 A1* 3/2018 Joseph .................. A61F 5/0118

* cited by examiner

*Primary Examiner* — Ophelia A Hawthorne
(74) *Attorney, Agent, or Firm* — Rivka Friedman (57) ABSTRACT

An adjustable limb stabilization device relates to an adjustable limb stabilization device for supporting a body part. More specifically the present invention is directed to an orthosis adapted to accommodate a predetermined orientation for a body part relative to a surface. an adjustable limb stabilization device comprising of a lateral slab 1, a first mechanical fastener 2 adapted to tighten and loosen the adjustable limb stabilization device and a connector assembly 3 adapted to pivotally adjoin the lateral slab 1 for supporting an injured limb. The connector assembly 3 may be a continuously molded connecting membrane, a hinge, a crease, or any other suitable component. Moreover, a fastener mechanism connects two or more said stabilization device 100 as per requirement.

8 Claims, 12 Drawing Sheets

ADJUSTABLE LIMB STABILIZATION DEVICE

FIELD OF INVENTION

The present invention generally relates to an adjustable limb stabilization device for supporting a body part. More specifically the present invention is directed to an orthosis adapted to accommodate a predetermined orientation for a body part relative to a surface.

BACKGROUND OF THE INVENTION

Injuries to the limbs, particularly fractures of the hands, arms and wrist are commonly treated by the use of a cast or other brace that supports the injured limb and in certain cases prevents the limb from rotating around the wrist or other applicable joint. These injuries include sprains, fractures, contusions and other injuries that are common and frequent and, unless properly treated, recurrent.

Certain injuries, particularly limb fractures, result in the limb becoming misaligned with respect to its normal position. To treat such a fracture, the physician must appropriately align the fractured limb then apply a support suitable to stabilize the limb during healing. Braces commonly used to maintain reduction of a fracture or otherwise treat an injured limb include plaster casts prepared by a physician and applied by forming the plaster about the patient's limb. Plaster casts of this type are generally heavy, bulky and easily broken. Moreover, because the material is sensitive to water and underpadding attracts or absorbs water, it is not possible to wash the cast and due to the fact that the material is opaque, it is impossible to allow any direct viewing of the skin absent the removal thereof. Cast made up from plaster of Paris cause discomfort and other problems for the patient. For example, a typical compression cast is not adjustable, and therefore its position on the limb is fixed upon compression. This compression may be applied too tightly for some patients; it also may become too loosely attached over time as swelling in the arm recedes.

U.S. Pat. No. 4,323,061 discloses a cast substrate made from a combination of glass fibers and a second fiber such as cotton, flax, rayon, wool, acrylic resin, nylon, Teflon or polyester. The purpose of the second fiber in the substrate is to hold the curable resin on the substrate.

U.S. Pat. No. 3,332,416 discloses a plaster of Paris cast bandage with a woven substrate made with a combination of elastic and inelastic fibers.

All of these casting materials disclosed in prior-art having fiberglass with different reactive polymers suffer from certain disadvantages. One of the major disadvantages is the conformability of the casting tape to the body of the patient. Conformability is the characteristic of the casting tape which has been defined as that property which describes the ability of the bandage or casting tape to adapt to or intimately lay down against the compound curves and protrusions of a body member. This leads to requirement of applying plaster of paris as a primary casting material and fiberglass as a secondary casting tapes. Which makes the healing process time-intensive, labour-intensive and expensive as it involves cutting, aligning in a skilled way.

U.S. Pat. No. 5,492,133 A talks about an improved ankle support system including first and second support side walls and attaching straps which have an elongated hook portion pivotally attached to the side wall support and which has an elongated loop portion integrally formed with the hook portion and having a width wider than the loop portion such that when the strap is wrapped around the leg, the loop portion entirely covers the hook portion.

U.S. Pat. No. 5,653,244 A discloses a therapeutic compression garment made of flexible, foldable, light weight Velcro-type loop fabric having a central region for wrapping partially around a body part and a plurality of pairs of bands integrally connected to the central region and extending outwardly in opposite directions from both sides of the central region to encompass the body part.

A second set of problems arises with the support characteristics of this common type of orthopaedic support. First, the typical support stretches in order to roughly conform to the shape of joints and limbs. However, mere stretching cannot allow the support to closely conform to the nuances in the shape of the limb or joint, particularly in the case of knees, elbows and ankles. As a result, areas of the limb or joint are left under-supported or even entirely unsupported.

Another problem arises because the typical support has a base that is of uniform thickness and density, thereby producing uniform circumferential compression. Such compression cannot be increased or decreased to provide more or less support in selected areas of the injured limb or joint, in the absence of supplemental material straps. Consequently, such a support tends to shift position on the limb because there are no regions of high pressure to anchor it. Furthermore, a support having uniform thickness and density may allow the limb to move with equal ease in a variety of directions. Such ease of movement may increase the likelihood that a particular injury such as a patella injury will be aggravated.

U.S. Pat. No. 6,447,470 B2 teaches about Ready-to-use bandage self-adhesively coated on one side, for relieving, stabilizing and functionally restricting the ligament and muscle structures of the knee joint, comprising a substantially rectangular central part (A) which is at least partially inelastic in the transverse direction of the bandage and on which there are respectively arranged, directed upwards and downwards seen in the longitudinal direction, two elongate strips (B, C, D and E).

A third set of problems arises with respect to the performance of the typical support. One problem is that the support material tends to bunch up whenever the limb is flexed. This bunching tends to interfere with the motion of the limb, is uncomfortable to the user, and may rub or chafe the skin and even bruise the skin. Another problem is that the edges of the typical support are die-cut, thereby exposing the user's skin to potentially allergenic support materials, such as neoprene. The edges tend to be rather rough, causing skin irritation during exercise.

An additional set of problems stems from hardware that may be attached to the typical support. Such hardware may include gel packs, inflatable bladders, pumps, straps, and struts. This hardware tends to protrude from the base of the support and can get caught on other objects. Since the hardware is typically sewn onto the base, the stitches can be ripped from the base and the hardware torn free. A special problem arises with hinged strut mechanisms, which can be twisted out of place so that the hinged strut does not properly guide and support the flexing motion of the joint.

Thus, it is desirable to have limb stabilization device that allows greater flexibility in the function of the brace while still providing adequate support for the injured limb, particularly in the treatment of limb fractures.

SUMMARY OF THE INVENTION

The present invention discloses an adjustable limb stabilization device which addresses deficiencies in the prior—art by providing in various embodiments capable of stabilizing an injured limb. The device is also suitable for treatment of injuries arising from fracture, sprain, contusion, or other injuries to the limb. In certain embodiments the device fits across and substantially immobilizes the injured limb.

The principal object of the present invention is to provide an adjustable limb stabilization device comprising of a lateral slab 1, a first mechanical fastener 2 adapted to tighten and loosen the adjustable limb stabilization device and a connector assembly 3 adapted to pivotally adjoin the lateral slab 1 for supporting an injured limb. The connector assembly 3 may be a continuously molded connecting membrane, a hinge, a crease, or any other suitable component. Moreover, a fastener mechanism connects two or more said stabilization device 100 as per requirement.

The other object of an invention is to provide an adjustable limb stabilization device comprising of a lateral slab 1 is made of flexible material consisting of silicone rubber, latex rubber, synthetic rubber or any combination thereof adapted for patient comfort. Lateral slab can be customizable interlaced structure having an isolated layer with hollow tube structure.

The other object of an invention is to provide an adjustable limb stabilization device comprising of a lateral slab 1 is flat unfolded geometry with varied configuration sizes i.e. design and shape to result in the relief, fixing, stabilization and/or functional restriction of the limb and can be applied by the user in a simple way.

The other object of an invention is to provide an adjustable limb stabilization device comprising of a lateral slab 1 is capable to have at least one entrant infusion material. Entrant infusion material can be selected from a group consisting of low viscosity epoxy material that includes epoxy resins, acrylate fillers and activators, polyurethane, polymer or any combination thereof. Entrant infusion material can be introduced under pressure into customizable interlaced structure having an isolated layer with hollow tube structure before or after applying lateral slab 1 to an injured limb.

The other object of an invention is to provide an adjustable limb stabilization device comprising of a first mechanical fastener 2 is loop portion of a hook and loop fastener for tightening and loosening the adjustable limb stabilization device for locking the lateral slab 1 with body part.

The other object of an invention is to provide an adjustable limb stabilization device comprising of a connector assembly 3 are flexible straps containing both hook and loop releasable fastening elements and that is capable of attaching to lateral slab 1.

The other object of an invention is to provide an adjustable limb stabilization device with stabilizing process of entrant infusion material by means of external light source or thermal curing at room temperature or chemical reaction curing.

Another object of the present invention is to provide an adjustable limb stabilization device can be joint together by means of fastener mechanism as per requirement.

The other object of an invention is to provide an adjustable limb stabilization device by means of providing improved support system for an injured limb which is flexible, non-opaque, and non-allergic and user friendly.

These and other objects, advantages and features result from the following description of a preferred embodiment of an adjustable limb stabilization device of the invention disclosed by way of non-limitative example in the figures of the accompanying drawings.

DETAILED DESCRIPTION OF THE INVENTION

Present invention eliminates the disadvantages of prior art orthopaedic casts, cast material, orthopaedic support methods and devices and to provide an adjustable limb stabilization device for stabilizing an injured limb. The present invention provides an improved support system having user friendly properties like flexibility, non-opaqueness and skin friendly for an injured limb.

The principle embodiment of the invention is to provide an adjustable limb stabilization device 100 comprising of a lateral slab 1, a first mechanical fastener 2 adapted to tighten and loosen the adjustable limb stabilization device and a connector assembly 3 adapted to pivotally adjoin the lateral slab 1 for supporting an injured limb. The connector assembly may be a continuously molded connecting membrane, a hinge, a crease, or any other suitable component.

Another principal embodiment of the present invention is to provide an adjustable limb stabilization device 100 is able to joint together by means of fastener mechanism as per requirement.

One of the embodiments of an invention is to provide an adjustable limb stabilization device 100 comprising of a lateral slab 1 is made of flexible material consisting of silicone rubber, latex rubber, synthetic rubber or any combination thereof adapted for patient comfort. Lateral slab can be customizable interlaced structure having an isolated layer with hollow tube structure 04. The advantages of the present invention are numerous and significant. Because of the lateral slab 1 can be made of silicone rubber, latex rubber, synthetic rubber or any combination thereof, it can be clear so that the portion of the body to be surrounded can be viewed during the initial fitting of the cast.

One of the embodiments of an invention is to provide an adjustable limb stabilization device comprising of a lateral slab 1 is flat unfolded geometry with varied configuration sizes i.e. design and shape to result in the relief, fixing, stabilization and/or functional restriction of the limb and can be applied by the user in a simple way. The design pattern of the lateral slab 1 is preferably net-like in appearance to permit biaxial stretching both vertically and horizontally. Alternatively, the design pattern can be either a lattice-like pattern or quadrille to permit biaxial stretching along diagonal axes.

One of the embodiments of an invention is to provide an adjustable limb stabilization device 100 comprising of a lateral slab 1 is capable to have at least one entrant infusion material. Entrant infusion material can be selected from a group consisting of low viscosity epoxy material that includes epoxy resins, acrylate fillers and activators, polyurethane, polymer or any combination thereof. Entrant infusion material can be introduced under pressure into customizable interlaced structure having an isolated layer with hollow tube structure 04 before or after applying lateral slab 1 to an injured limb. In accordance with the method of the present invention, a portion of the body to be held immobile is surrounded with lateral slab 1 with the help of connector assembly 3 and the lateral slab is filled with the entrant infusion material which is flowable and hardenable material and releasably retained in place until the material hardens and the volume of the nonhardening fluid can be adjusted. The lateral slab 1 allows variable adjustment of the support to the limb and which is self-equilibrating. When the hardenable material finally hardens it will give uniform circumferential pressure to the fracture site thus providing pressure which is always automatically equilibrated and remains so even while providing ventilation. The uniform circumferential hydrostatic pressure keeps the bone or bones in place while healing and uniformity is important to avoid pressure spots leading to sores.

One of the embodiments of an invention is to provide an adjustable limb stabilization device 100 comprising of a first mechanical fastener 2 is loop portion of a hook and loop fastener for tightening and loosening the adjustable limb stabilization device for locking the lateral slab 1 with body part. Hook and loop fasteners are now commercially available with firm yet stretchable loop portions of various thicknesses and a broad range of elastic properties. The elastic properties provided by the stretchable loop portion make it possible for an adjustable limb supporting device to be effectively wrapped as few as one turn around a part of the body while maintaining contact of lateral slab 1 with the skin to be treated. For example, a single loop handle can be connected to the lateral slab 1 adjacent to the first and second straps. Or else two loop handles are provided, one extending between an intermediate portion of the lateral slab 1 and the first strap and the other extending between the intermediate portion of the lateral slab 1 and the second strap or the loop handles are secured to the lateral slab 1 so as to provide the most effective leverage for the user for lifting the limb supporting device. The length of the lateral slab 1 varies not only dependent upon the size of the person, but also whether the first and second straps are to be connected to the body parts to be treated. The connector assembly of the device according to present invention can be constructed of nylon webbing, a hook-and-loop material known as Velwrap™, and D-rings with sewable tabs. As a result of the use of the hook-and-loop material, the first and second straps can be appropriately adjusted in size to fit the body parts to be treated.

Figure 1:
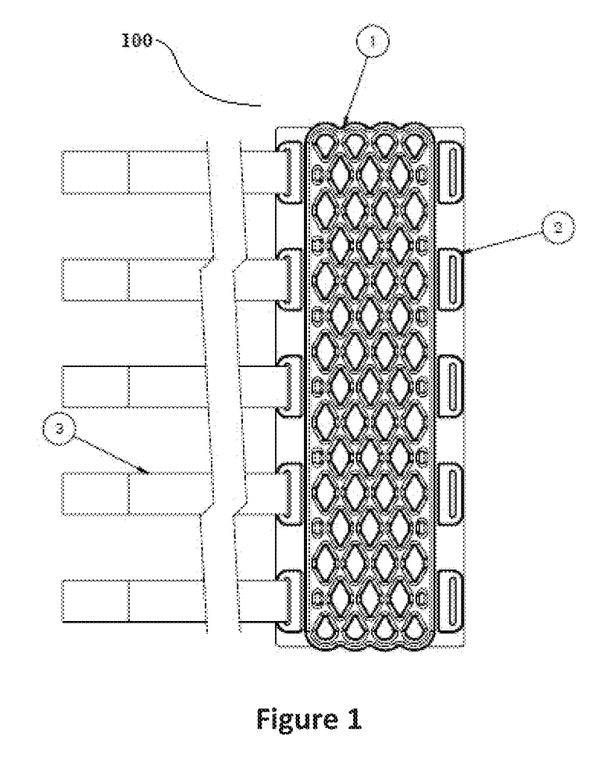
FIG. 1: Depicts top-view of an adjustable limb stabilization device according to present invention.
Figure 2:
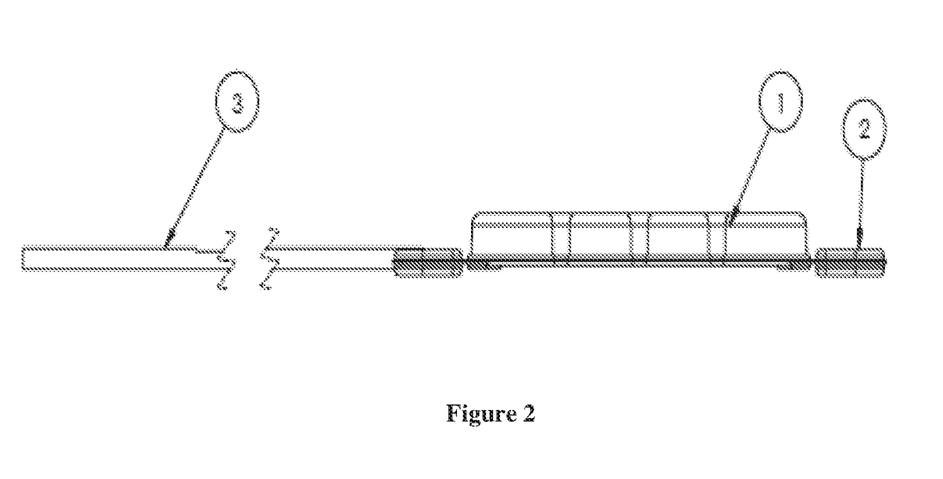
FIG. 2: Depicts front-view of an adjustable limb stabilization device according to present invention.
Figure 3:
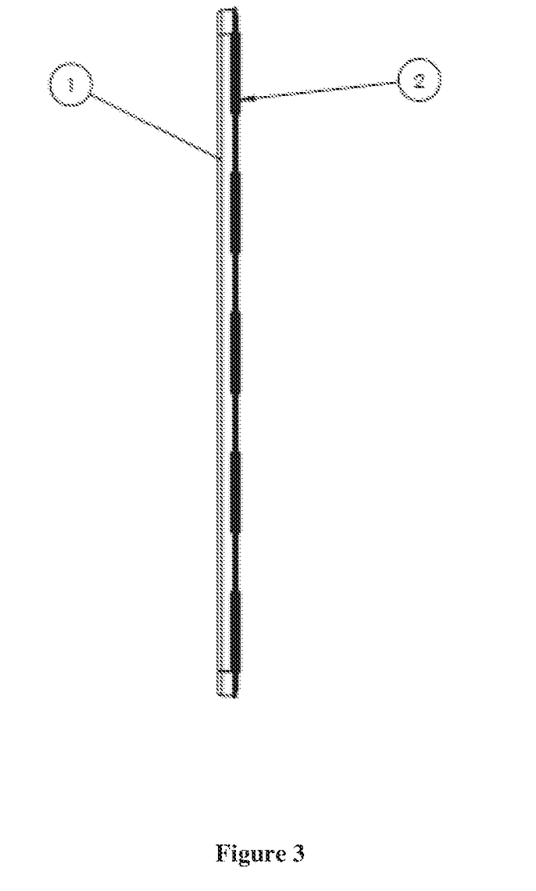
FIG. 3: Depicts side-view of an adjustable limb stabilization device according to present invention.
Figure 4:
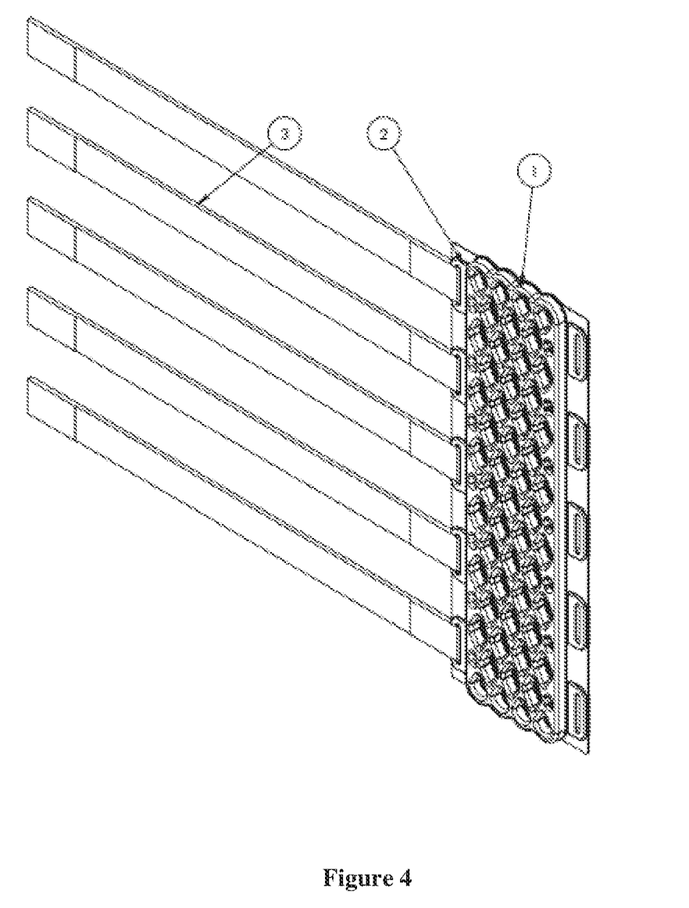
FIG. 4: Depicts isometric-view of an adjustable limb stabilization device according to present invention.
Figure 5:
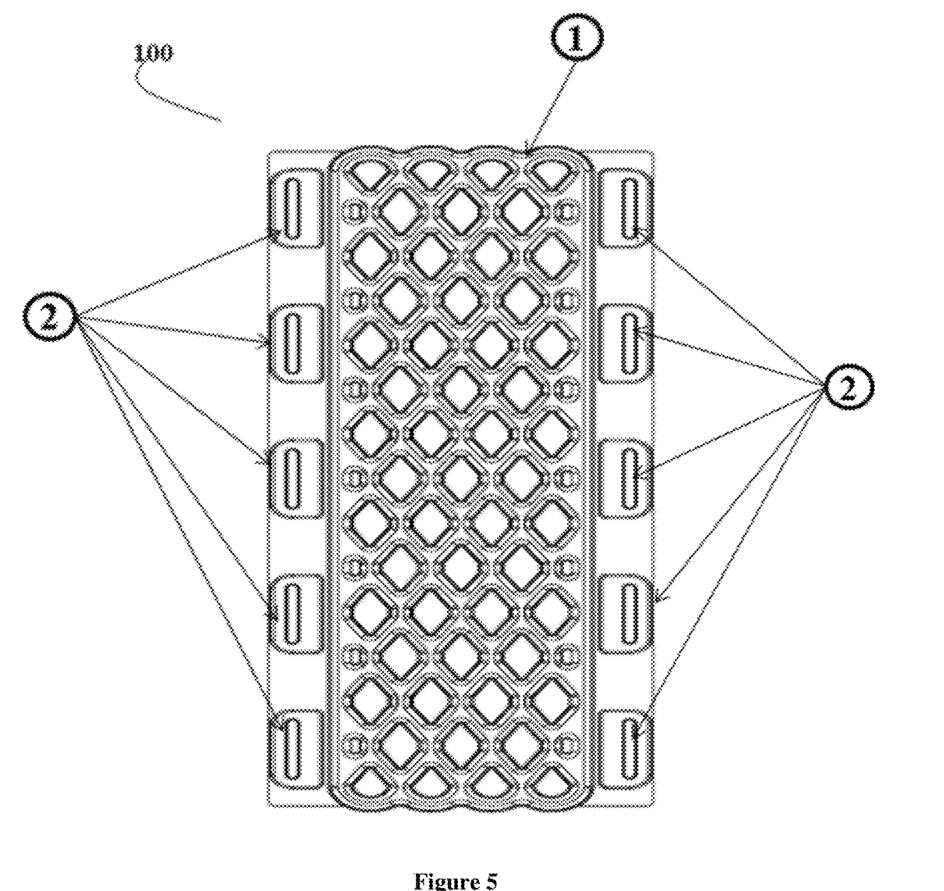
FIG. 5: Depicts top-view of an adjustable limb stabilization device without connector assembly according to present invention.
Figure 6:
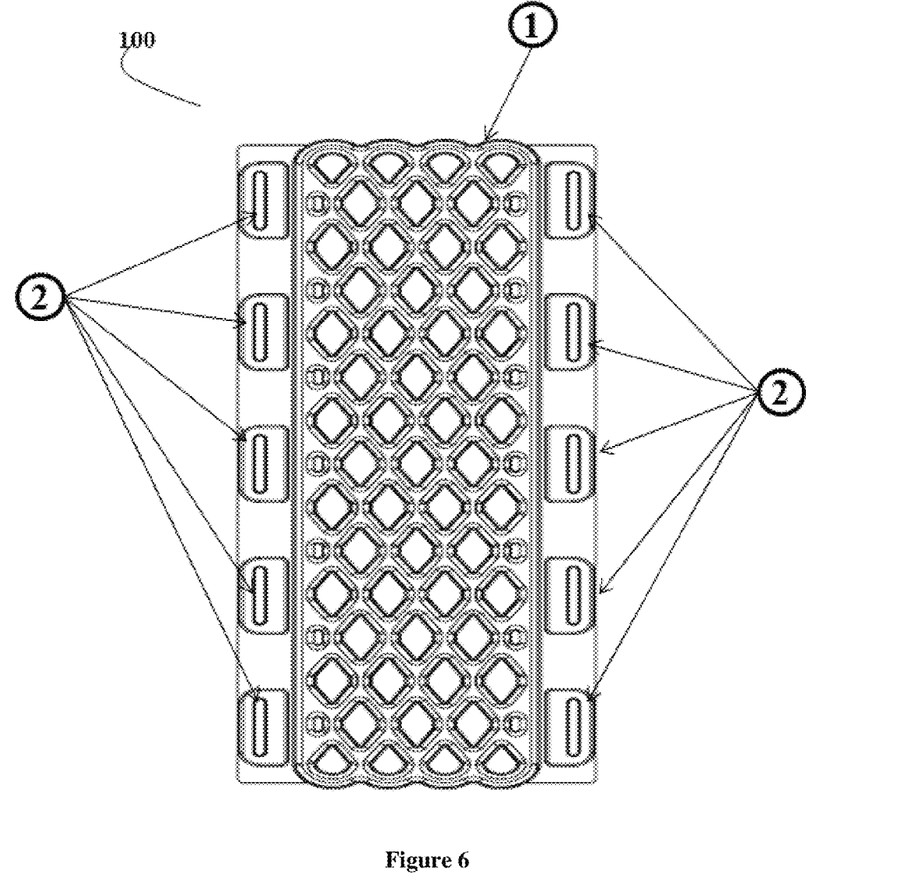
FIG. 6: Depicts bottom-view of an adjustable limb stabilization device without connector assembly according to present invention.

One of the embodiments of an invention is to provide an adjustable limb stabilization device 100 comprising of a connector assembly 3 are flexible straps containing both hook and loop releasable fastening elements and that is capable of attaching to lateral slab 1. Referring to FIG. 5 and FIG. 6 which depicts the top and bottom view of the device without connector assembly. For example, the limb supporting device used for leg may use an upper strap for encircling an upper portion of the leg (nearer the torso) and a lower strap for encircling a lower portion of the leg (nearer the foot) interconnecting with the lateral slab 1 configured into a loop-like structure.

One of the embodiments of an invention is to provide an adjustable limb stabilization device 100 with stabilizing process of entrant infusion material by means of external light source or thermal curing at room temperature or chemical reaction curing. For example, lateral slab 1 can be filled with fast hardening clear epoxy and wrapped around the arm of a patient. An adjustable limb supporting device is held in the wrapped position and covered by black coloured tape and is allowed to be adjusted to body part for five minutes. After that the black coloured tape is removed. After removing the tape, the lateral slab is exposed to daylight and will be cured thermally at room temperature. The curing process can be expedited using any kind of light source.

One of the embodiments of an invention is to provide an adjustable limb stabilization device 100 by means of providing improved support system for an injured limb which is flexible, non-opaque, and non-allergic and user friendly. In addition, present invention offers a beneficial combination of advantages for use in exercise and sports activities by simultaneously providing muscular-skeletal support, flexibility, comfort, ease of adjustment by providing ventilation due to its aesthetic design to the body part under treatment. Present invention is an improvement over the prior limb supporting methods by providing substantial orthopaedic support with a limited number of wraps, an adjustable device is more durable as materials for connecting assembly than thin elastic based products commonly available, both pressure and silicone therapies may be applied concomitantly and therefore eliminating a separate and/or repeated process of fitting more than one material individually, patient compliance may be improved because continued and repeated, even long term, comfortable use of the device is possible without loss of support from the lateral slab 1 while in placement and in use, the device according to present invention resists slippage, migration and unintended movement while in use and the device according to present invention does not adhere to the skin nor does it significantly pull hair or fur when it is removed from use. Furthermore, the present invention provides the added benefit of a supporting device that supplies even pressure to the body across the area being treated. A strip of a complimentary hook portion of the hook and loop fastener provides quick and simple closure of the wrap about the body part while maintaining effective wrap placement of the device even during strenuous activity and/or flexing of the body.

Figure 7:
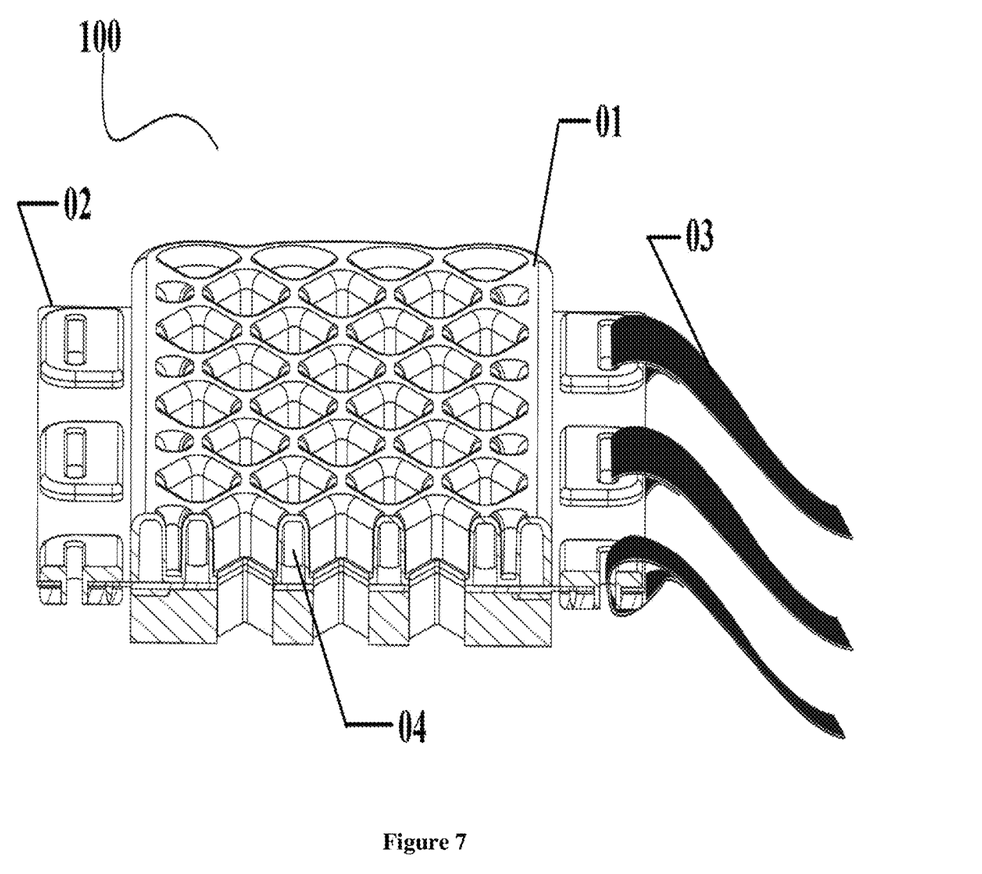
FIG. 7: illustrate cross-sectional view of an adjustable limb stabilization device having hollow tubing.
Figure 8:
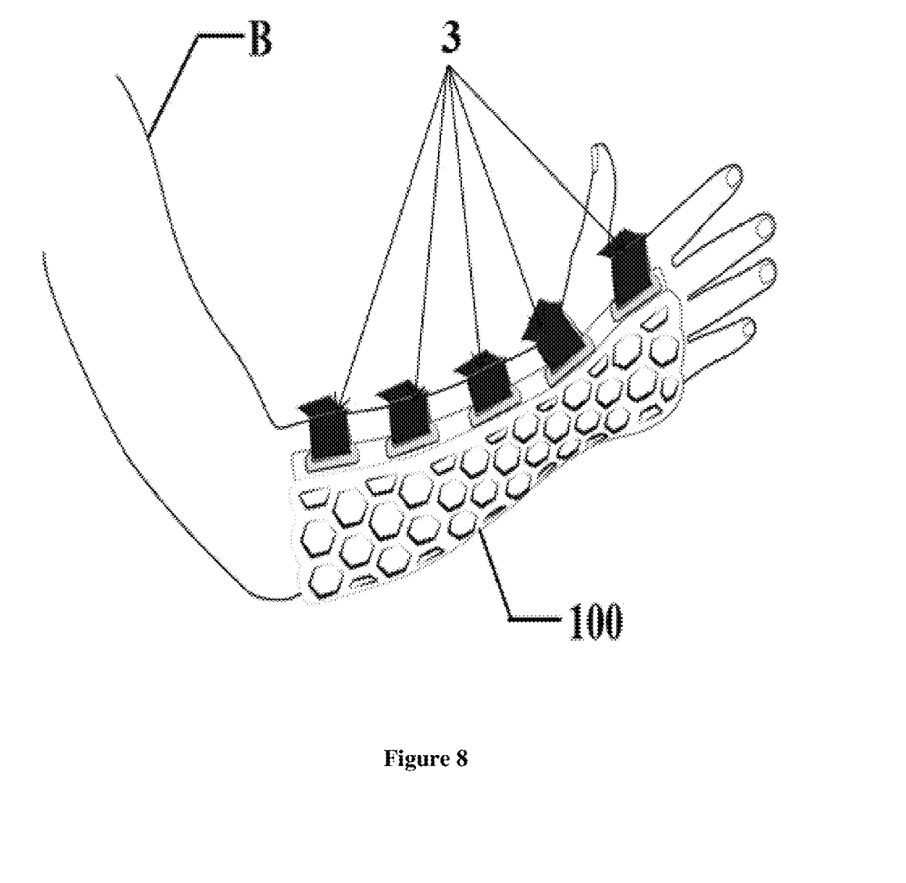
FIG. 8: discloses an application of an adjustable limb stabilization device to the human body.

FIG. 7 of the present invention discloses a cross sectional view of an adjustable limb device wherein, hollow tubing 4 structure of said device is filled with curable composite material. FIG. 8 of the present invention discloses an adjustable limb device 100 is apply to human body B at fracture limb.

Figure 9:
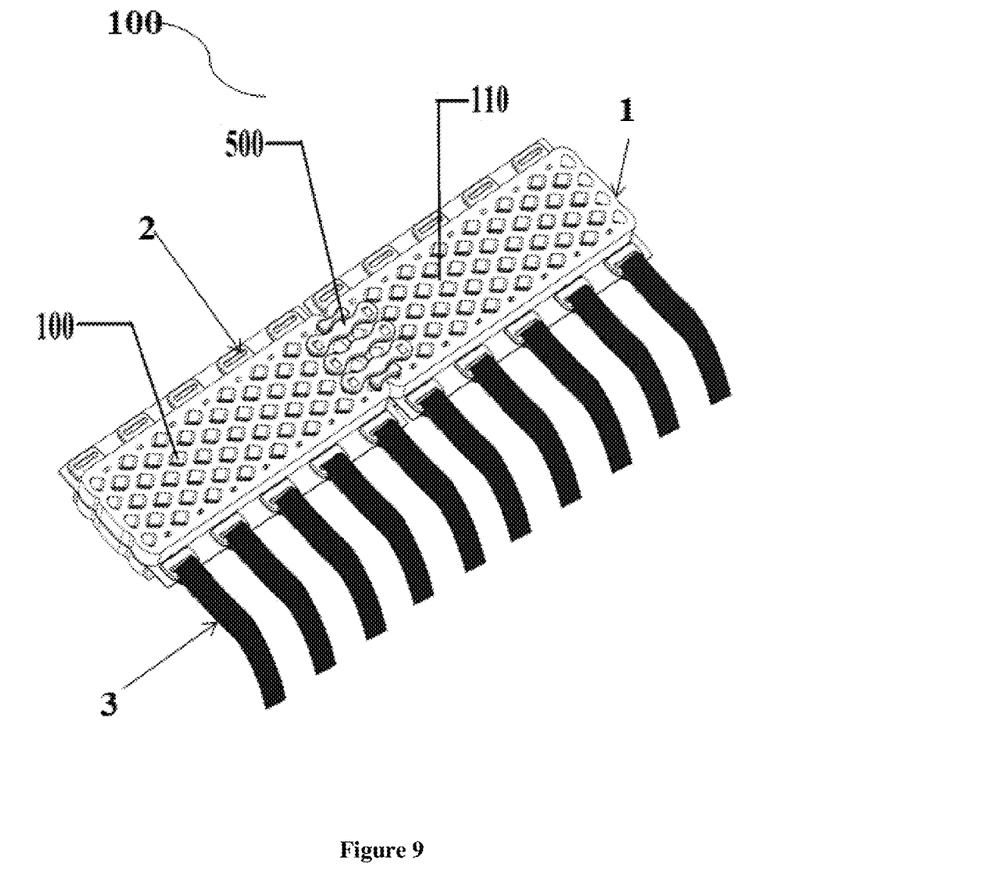
FIG. 9: discloses an embodiment wherein two or more said limb stabilization device are connected by means of fastener mechanism.

FIG. 9 of the present invention discloses an embodiment wherein device fastener mechanism 500 comprises cap strips 510 and socket strips 520 which connects two or more adjustable limb device with each other. Size and number of cap strips 510 and socket strip 520 vary as per requirement. For an example in FIG. 9, one adjustable limb device 100 and second adjustable limb device 110 are connected by means of device fastener mechanism 500.

Figure 10:
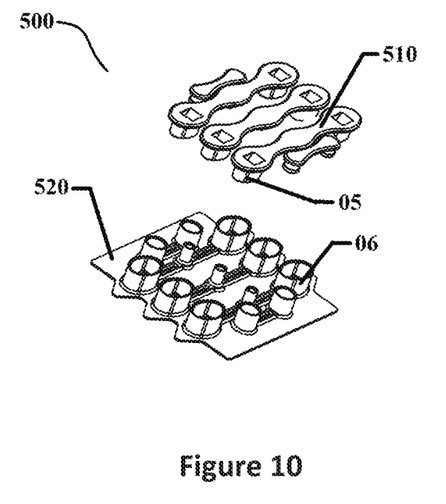
FIG. 10: discloses a device fastener mechanism.
Figure 10A:
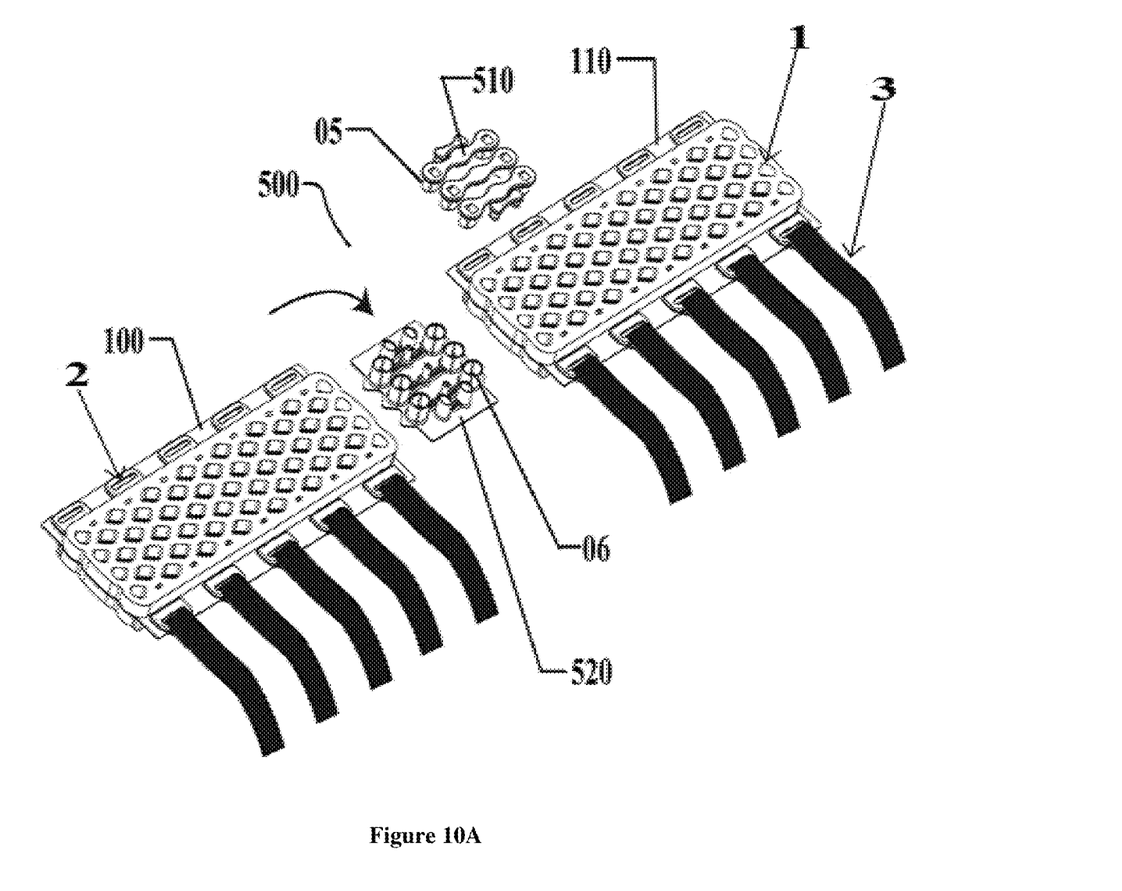
FIG. 10A: discloses exploded view of two limb stabilization device are connected with each other.

FIG. 10 of the present invention discloses a device fastener mechanism 500 comprises more than one cap strips 510 comprises more than one eyelet 05 and socket strips 520 comprises more than one hollow stud 06. Eyelet 05 of cap strip 510 and hollow stud 06 of socket strips 520 are locked. The word "Eyelet" discloses herein as a solid or hollow cylinder object having small diameter than hollow stud 06 wherein said eyelet 05 can lock into hollow stud 06 by applying force onto said eyelet 05. The word "hollow stud" discloses herein as a hollow cylindrical object having larger diameter than eyelet 05 and lock eyelet 05 into a hollow cylinder structure of said stud 06. FIG. 10A of the present invention illustrate an exploded view wherein one adjustable limb device 100 and second adjustable limb device 110 are connected by means of device fastener mechanism 500. Further, the position of eyelet and hollow stud may be vice-versa said it is very obvious to change the position of eyelet and hollow stud means eyelet 05 can attached with socket strips 520 and also hollow stud 06 can be attached with cap strip 510, too for person skilled in the art.

Figure 11:
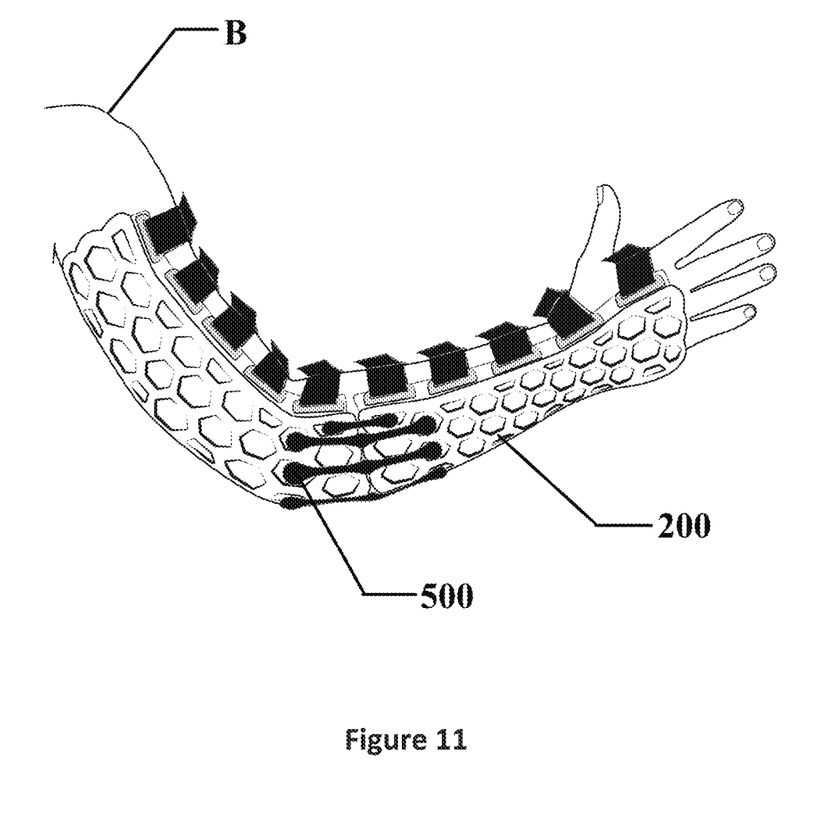
FIG. 11: illustrate an embodiment of the present invention which is extendable as per requirement.

FIG. 11 of the present invention discloses an application of expanded adjustable limb stabilization device 200 to human body B wherein one adjustable limb device 100 and second adjustable limb device 110 are connected by means of device fastener mechanism 500.

One of the embodiments of an invention is to provide an adjustable limb stabilization device to allow a physician or patient to do monitoring as well dressing of the wound without removing the device in case of accidental injuries.

The invention has been described with reference to the illustrated preferred embodiments. The invention is not unduly limited by this disclosure of the preferred embodiment described, instead it is intended that the invention be defined as their equivalents.

I claim:

1. An adjustable limb stabilization device (100), comprising: a lateral slab (01) comprising a hollow tube structure (04) having one or more openings each opening configured to receive an infusion material;
   a first mechanical fastener (02) provided on a first side of the lateral slab (01), and
   a connector assembly (03) comprising a flexible strap provided on a second side opposite to the first side of the lateral slab (01), configured to releasably connect with a corresponding mechanical fastener (02);
   wherein upon engagement, the mechanical fastener (02) is connected with the corresponding connector assembly (03) wherein the connector assembly (03) comprising the flexible strap is adapted to cooperatively tighten and loosen the adjustable limb stabilization device around a limb;
   wherein the adjustable limb stabilization device comprises a first adjustable device (100) and second adjustable device (110) connected to each other with a fastener mechanism (500), comprising at least one cap strip (510) and at least one socket strip (520), wherein the cap strip (510) and socket strip (520) are designed to connect the first adjustable limb device (100) and the second adjustable limb device (110).

2. The adjustable limb stabilization device (100) as claimed in claim 1, wherein the lateral slab (01) is made of a flexible material consisting of at least one of silicone rubber, latex rubber, synthetic rubber or any combination thereof.

3. The adjustable limb stabilization device (100) as claimed in claim 1, wherein the entrant infusion material is selected from the group consisting of low viscosity epoxy materials, epoxy resins, acrylate fillers and activators, polyurethane, polymer or any combination thereof.

4. The adjustable limb stabilization device (100) as claimed in claim 1, wherein the lateral slab (01) comprises a flat unfolded geometry.

5. The adjustable limb stabilization device (100) as claimed in claim 1, wherein the entrant infusion material is configured be introduced under pressure into the one or more openings before or after applying the lateral slab (01) to the limb.

6. The adjustable limb stabilization device (100) as claimed in claim 1, wherein the lateral slab (01) is at least one of: non-opaque, and non-allergic.

7. The adjustable limb stabilization device (100) as claimed in claim 1, wherein the adjustable limb stabilization device (100) is configured to be connected to additional adjustable limb stabilization device by means of the device fastener mechanism (500).

8. An adjustable limb stabilization system, comprising:
   a first adjustable limb stabilization device (100) and a second adjustable limb stabilization device (110), each of the first adjustable limb stabilization device (100) and the second adjustable limb stabilization device (110) comprising:
   a lateral slab (01) comprising a hollow tube structure (04) having one or more openings, wherein each of the one or more openings are configured to receive an entrant infusion material;
   and
   a connector assembly (03) provided on a second side opposite to the first side of the lateral slab (01), configured to releasably connect with the corresponding mechanical fastener (02),
   wherein upon engagement, the mechanical fasteners (02) are connected with the corresponding connector assembly (03) wherein the connector assembly (03) comprising a flexible strap is adapted to cooperatively tighten and loosen the adjustable limb stabilization device around a limb; and
   a device fastener mechanism (500) for connecting the first adjustable limb stabilization device (100) to the second adjustable limb stabilization device (110), the device fastener mechanism (500) comprising:
   a first adjustable stabilization device (100) with a cap strip (510) having at least one eyelet (05) the second adjustable limb stabilization device (110), with a socket strip (520) having at least one hollow stud (06),
   wherein the at least one eyelet (05) of the cap strip (510) is configured to align with and lock into the at least one hollow stud (06) of the socket strip (520), thereby connecting the first adjustable limb stabilization device (100) to the second adjustable limb stabilization device (110).

* * * * *